United States Patent
Sachdeva et al.

(10) Patent No.: US 11,179,334 B1
(45) Date of Patent: Nov. 23, 2021

(54) TARGETED CARRIERS FOR TACROLIMUS FOR OCULAR INFLAMMATION

(71) Applicant: Florida A&M University, Tallahassee, FL (US)

(72) Inventors: Mandip Sachdeva, Tallahassee, FL (US); Imran Vhora, Tallahassee, FL (US); Shallu Kutlehria, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 47 days.

(21) Appl. No.: 16/780,553

(22) Filed: Feb. 3, 2020

Related U.S. Application Data

(60) Provisional application No. 62/800,628, filed on Feb. 4, 2019.

(51) Int. Cl.
| | |
|---|---|
| *A61K 9/107* | (2006.01) |
| *A61K 31/436* | (2006.01) |
| *A61K 47/36* | (2006.01) |
| *A61K 47/34* | (2017.01) |

(52) U.S. Cl.
CPC .......... *A61K 9/1075* (2013.01); *A61K 31/436* (2013.01); *A61K 47/34* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 2009/0011018 A1* | 1/2009 | Kondo | A61K 9/2018 424/472 |
| 2009/0092665 A1* | 4/2009 | Mitra | A61P 27/04 424/450 |
| 2011/0217377 A1* | 9/2011 | Zale | A61K 31/337 424/484 |

FOREIGN PATENT DOCUMENTS

| | | | | |
|---|---|---|---|---|
| WO | WO-2017019214 A1 * | 2/2017 | | A61P 37/06 |

OTHER PUBLICATIONS

Kymionis et al., Treatment of chronic dry eye: focus on cyclosporine. Clinical Ophthalmology. 2008. vol. 2 (No. 4): 829-836.
Taravati et al., Postcataract surgical inflammation. Current opinion in ophthalmology. 2012. vol. 23 (No. 1): 12-18.
Dua and Attre. Treatment of Post-operative Inflammation following Cataract Surgery—A Review. European Ophthalmic Review. 2012. vol. 6: 98-103.
Saha et al., Existence of a p-glycoprotein drug efflux pump in cultured rabbit conjunctival epithelial cells Investigative Ophthalmology & Visual Science. 1998. vol. 39 (No. 7): 1221-1226.
Kawazu et al., Characterization of cyclosporin A transport in cultured rabbit corneal epithelial cells: P-glycoprotein transport activity and binding to cyclophilin. Investigative Ophthalmology & Visual Science. 1999. vol. 40 (No. 8): 1738-1744.

(Continued)

*Primary Examiner* — Kyung S Chang
(74) *Attorney, Agent, or Firm* — Smith & Hopen, P.A.; Michele L. Lawson

(57) ABSTRACT

A formulation and method for treating or reducing ocular surface inflammation and associated diseases and disorders. The formulation includes targeted micelles that encapsulate tacrolimus within a pharmaceutically acceptable carrier, wherein the formulation is coated in arginine-glycine-aspartic acid peptide.

20 Claims, 14 Drawing Sheets

(56) References Cited

OTHER PUBLICATIONS

Dey et al., Pharmacokinetics of erythromycin in rabbit corneas after single-dose infusion: role of P-glycoprotein as a barrier to in vivo ocular drug absorption. The Journal of Pharmacology and Experimental Therapeutics. 2004. vol. 311 (No. 1): 246-255.
Dey et al., Molecular evidence and functional expression of P-glycoprotein (MDR1) in human and rabbit cornea and corneal epithelial cell lines. Investigative Ophthalmology & Visual Science. 2003. vol. 44 (No. 7): 2909-2918.
STEPP. Corneal integrins and their functions. Experimental Eye Research. 2006. vol. 83: 3-15.
Elner & Elner. The integrin superfamily and the eye. Investigative Ophthalmology & Visual Science. 1996. vol. 37 (No. 5): 696-701.
Lauweryns et al., Distribution of very late activation integrins in the human cornea. An immunohistochemical study using monoclonal antibodies. Investigative Ophthalmology & Visual Science. 1991. vol. 32 (No. 7): 2079-2085.
Ley et al., Integrin-based therapeutics: biological basis, clinical use and new drugs. Nat Rev Drug Discov. 2016. vol. 15 (No. 3): 173-183.
Kunath et al., Integrin targeting using RGD-PEI conjugates for in vitro gene transfer. The Journal of Gene Medicine. 2003. vol. 5: 588-599.
Zin et al., A mouse dry eye model induced by topical adminisliation of benzalkonium chloride. Molecular Vision. 2011. vol. 17: 257-264.
Kutlehria, Shallu et al. Tacrolimus Loaded PEG-Cholecalciferol Based Micelles for Treatment of Ocular Inflammation. Pharm Res. Apr. 16, 2018;35(6):117. doi: 10.1007/s11095-018-2376-7. PMID: 29663141.

\* cited by examiner

TARGETED CARRIERS FOR TACROLIMUS FOR OCULAR INFLAMMATION

CROSS-REFERENCE TO RELATED APPLICATIONS

This non-provisional application is a continuation of and claims priority to provisional application No. 62/800,628, entitled "TARGETED CARRIERS FOR TACROLIMUS FOR OCULAR INFLAMMATION," filed Feb. 4, 2019 by the same inventors.

BACKGROUND OF THE INVENTION

1. Field of the Invention

This invention relates, generally, to ocular surface inflammation. More specifically, it relates to targeted tacrolimus formulations for treatment of ocular surface inflammation.

2. Brief Description of the Prior Art

Ocular surface inflammation is regarded as the most common ocular condition that is implicated in a variety of ocular diseases and conditions-including dry eye, corneal inflammation after ocular surgeries (e.g., LASIK, cataract, etc.), keratitis, conjunctivitis, etc. [1]. Mainstay therapies are usually anti-inflammatory drops and include NSAIDs, corticosteroids, and other drugs (e.g., cyclosporine (CsA), doxycycline) [1][2].

However, drawbacks of these conventional therapies include increased intraocular pressure, development of glaucoma [3], chronic administration (twice a day for up to 3 months), and high cost [1].

Further, pGP expression on corneal cells can lead to decreased efficacy and a chronic requirement for agents like CsA and tacrolimus-TAC [4][5][6][7]. Moreover, nasolacrimal drainage from ocular surface and poor corneal permeability add to the complications of conventional therapies.

Although certain topical tacrolimus formulations are currently being evaluated by The Eye Center and The Eye Foundation for Research in Ophthalmology (i.e., topical tacrolimus (0.01%) ophthalmic solution for in vernal keratoconjunctivitis; topical tacrolimus 0.05% eye drops), currently there is no effective formulation known for ocular targeted delivery of tacrolimus. Accordingly, what is needed is a formulation and corresponding treatment method for ocular targeted delivery of tacrolimus, where the formulation overcomes the shortcomings of the prior art. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an ophthalmic formulation for treating or reducing ocular surface inflammation is now met by a new, useful, and nonobvious invention.

The novel structure includes an ophthalmic formulation comprising targeted micelles that encapsulate tacrolimus in a pharmaceutically acceptable carrier. The pharmaceutically acceptable carrier may include gellan gum to enhance the retention time of the targeted micelles on the ocular surface. The formulation is coated in arginine-glycine-aspartic acid peptide to aid in targeting the nanoparticles to the corneal cells through $\alpha v$ integrins to enhance the nanoparticles uptake and retain the nanoparticles on the surface of the cornea. The micelles have a particle size of less than about 50 nm and entrapment efficiency of approximately 88.7%±0.9% w/w. In an embodiment, the micelles are targeted polymeric nanomicelles that are capable of sustained release of tacrolimus. In such an embodiment, the targeted polymeric nanomicelles have a particle size of less than about 100 nm and a drug encapsulation of greater than 99%. In yet another embodiment, the formulation further includes PLGA-PEG block copolymer.

The novel method of treating or reducing ocular surface inflammation includes administering a therapeutically effective amount of the targeted tacrolimus micelles in a pharmaceutically acceptable carrier to a patient—the targeted micelles including the details mentioned above.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

Figure 1:
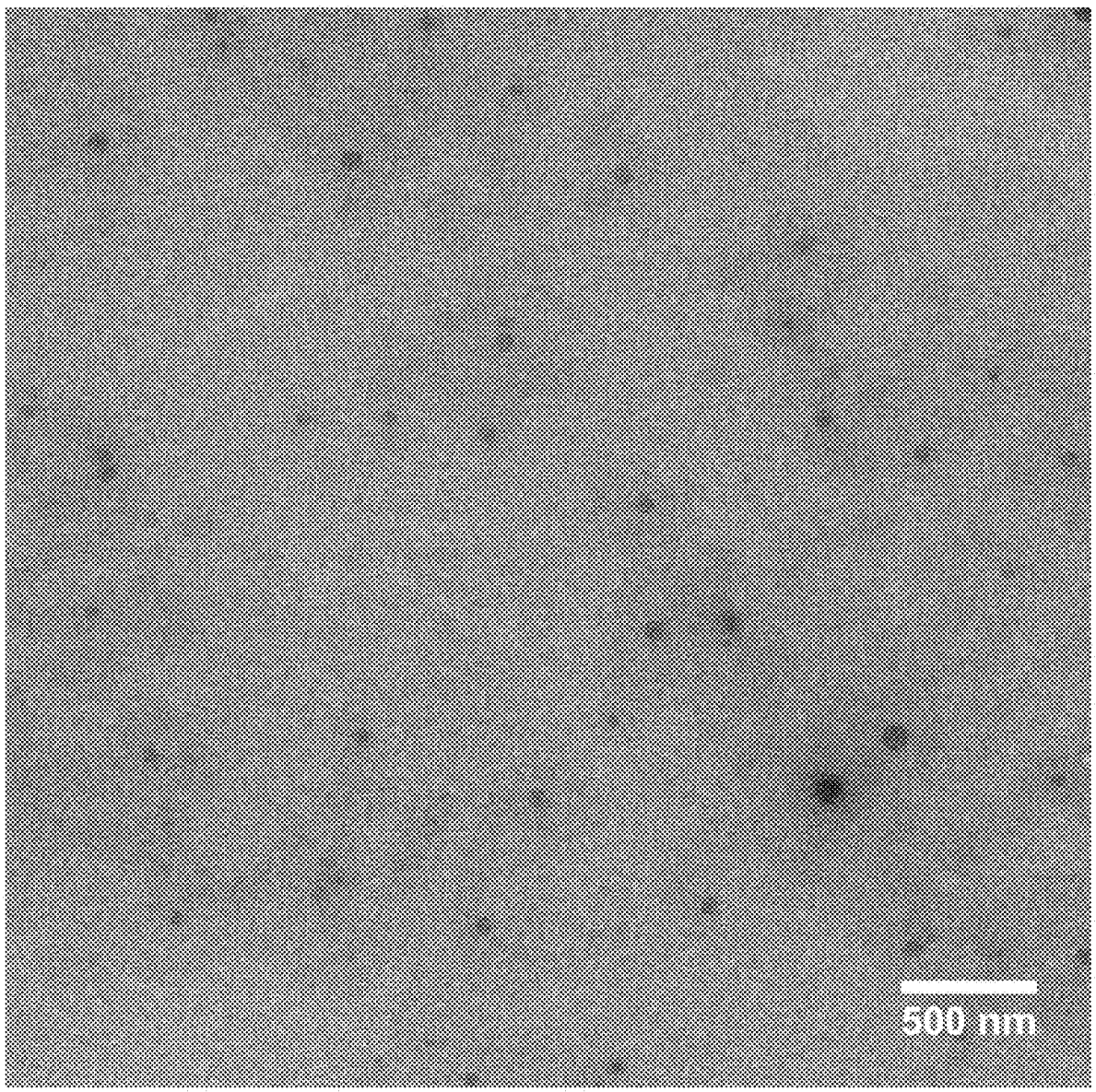
FIG. 1 is a TEM image of targeted tacrolimus micelles (TTM).

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

As used herein, "about" means approximately or nearly and in the context of a numerical value or range set forth means ±15% of the numerical. In an embodiment, the term "about" can include traditional rounding according to significant figures of the numerical value. In addition, the phrase "about 'x' to 'y'" includes "about 'x' to about 'y'."

As used herein, "treat," "treatment," "treating," and the like refer to acting upon a condition (e.g., ocular surface inflammation) with an agent (e.g., tacrolimus) to affect the condition by improving or altering it. The improvement or alteration may include an improvement in symptoms or an alteration in the physiologic pathways associated with the condition. The aforementioned terms cover one or more treatments of a condition in a patient (e.g., a mammal, typically a human or non-human animal of veterinary interest), and includes: (a) reducing the risk of occurrence of the condition in a subject determined to be predisposed to the condition but not yet diagnosed, (b) impeding the development of the condition, and/or (c) relieving the condition, e.g., causing regression of the condition and/or relieving one or more condition symptoms (e.g., reduction of ocular surface inflammation).

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition or symptom thereof and/or may be therapeutic in terms of a partial or complete cure or alleviation for a condition and/or adverse effect attributable to the condition.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

The term "therapeutically effective amount" as used herein describes concentrations or amounts of components such as agents which are effective for producing an intended result, including reduction of ocular surface inflammation. Compositions according to the present invention may be used to effect a favorable change in ocular surface inflammation, whether that change is an improvement, relieving to some extent one or more of the symptoms of the condition being treated, and/or that amount that will prevent, to some extent, one or more of the symptoms of the condition that the host being treated has or is at risk of developing, or a complete cure of the disease or condition treated.

The term "administration" or "administering" is used throughout the specification to describe the process by which a composition comprising tacrolimus as an active agent, are delivered to a patient or individual for therapeutic purposes. The composition of the subject invention and methodology in use thereof can be administered a number of ways including, but not limited to, parenteral (such term referring to intravenous and intra-arterial as well as other appropriate parenteral routes), subcutaneous, peritoneal, inhalation, vaginal, rectal, nasal, or instillation into body compartments.

Administration will often depend upon the amount of compound administered, the number of doses, and duration of treatment. In an embodiment, multiple doses of the agent are administered. The frequency of administration of the agent can vary depending on any of a variety of factors, such as amount or progression of inflammation, and the like. The duration of administration of the agent, e.g., the period of time over which the agent is administered, can vary, depending on any of a variety of factors, including patient response, etc.

The amount of the agent contacted (e.g., administered) can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and film-related factors. Optimization of such factors is well within the level of skill in the art, unless otherwise noted.

As used herein, the term "subject," "patient," or "organism" includes humans and mammals (e.g., mice, rats, pigs, cats, dogs, and horses). Typical hosts to which an agent(s) of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range.

In certain embodiments, the current invention includes topical nanomicelles of PEG2000 conjugated with cholecalciferol (PEGCCF). Integrin targeted tacrolimus loaded nanomicelles (TTM) were prepared by solvent diffusion evaporation method. The therapeutic potential of TTM was evaluated in benzalkonium chloride-induced ocular inflammation model in BALB/c mice. Corneal fluorescent staining and histopathological analysis of corneal sections were performed. TTM had a particle size of lower than 100 nm, high encapsulation efficiency (88.7±0.9% w/w) and osmolality of 292-296 mOsmol/Kg. TTM significantly reduced the corneal fluorescence as compared to tacrolimus suspension (TACS). H&E staining showed that TTM could restore corneal epithelial integrity, reduce stromal edema ($p<0.05$), and decrease the number of inflammatory cells ($p<0.01$) compared with TACS. Immunohistochemistry analysis demonstrated lower expression of Ki67 positive cells ($p<0.05$) and IL-6 throughout the cornea against TACS ($p<0.01$) and the control ($p<0.001$). TTM is an innovative delivery system for improving ocular inflammatory conditions providing a cost-effective and convenient dosage for patients.

Certain embodiments of the current invention overcome drawbacks of conventional therapies, related to drainage after administration and effectiveness of the drug, by including delivery systems with long retention and cellular targeting ability. For this purpose, targeted nanoparticles were prepared to interact with corneal cells. Several αv integrins (αvβ1, αvβ3, αvβ5, αvβ6, and αvβ8) are expressed in ocular cells including keratocytes, endothelial cells, epithelial cells, and fibroblasts [8] and are implicated in eye inflammation [9]. Arginine-glycine-aspartic acid (RGD) peptide can help in targeting nanoparticles to the corneal cells through αv integrins and enhance their uptake [10][11] and retain the nanoparticles on the surface of the cornea. The improved healing would provide reduced dosing periods by minimizing the duration of therapy-thus also improving patient convenience.

In certain embodiments, the current formulation is useful for ocular inflammation conditions such as dry eye, keratitis, keratoconjunctivitis, conjunctivitis, infection of eye, inflammation after ocular surgery (cataract surgery, corneal transplant, LASIK). The formulation may be RGD-coated and targeted for tacrolimus to treat ocular inflammation.

In certain embodiments, the smaller particle size of the micelles provides improved uptake of the encapsulated drug over-marketed tacrolimus suspension formulation. Additionally, the formulation provides healing in a short period of time compared to suspension formulation, which are being evaluated in clinical trials. The improved healing by the formulation will reduce the duration of therapy which improves patient compliance and reduces costs to patients.

EXAMPLE

Preparation and Characterization of Targeted Tacrolimus Formulations

TTM were prepared by solvent diffusion evaporation method using PEGCCF, DSPE-PEG2000 and DSPE-PEG2000-RGD for entrapment of TAC in the core of the nanomicelles. Particle size of the nanomicelles was <50 nm, PDI<0.3 (by dynamic light scattering-DLS) and zeta potential was −16.81±0.80 mV. The TTM was transparent and clear in appearance (FIG. 1) with high entrapment efficiency (88.7±0.9% w/w). Filtration of TTM was carried out through 0.2μ PES membrane filter and no changes in the assay of the nanomicelles were observed, indicating the possibility for sterilizing the formulation by membrane filtration. The osmolality of TTM was 292-296 mOsmol/Kg and pH was 5.6±0.2. TEM images of the micelles showed spherical shape and concordance with the particles size, determined by DLS.

Figures 2A, 2B:
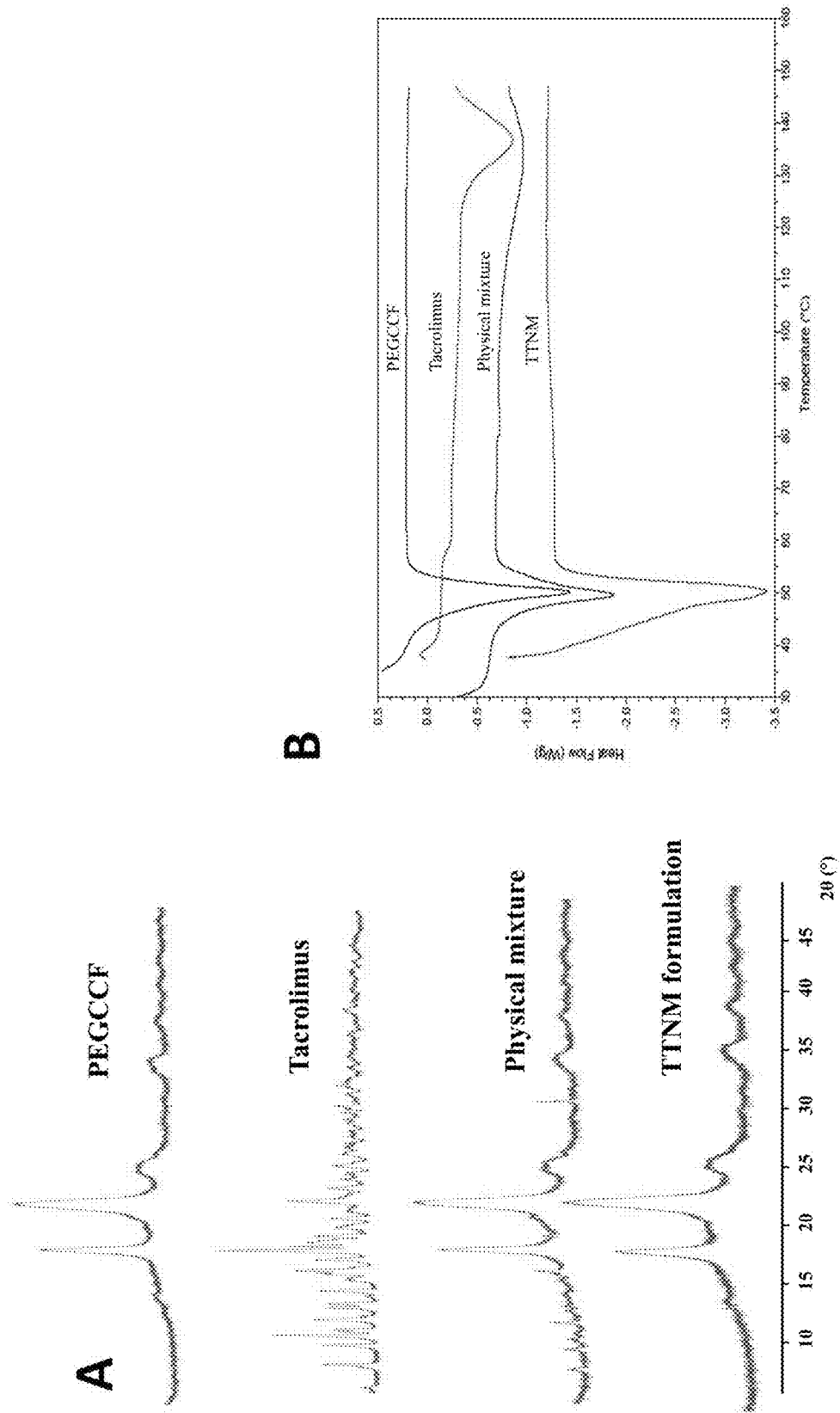
FIG. 2A depicts XRPD data of PEGCCF, TAC, physical mixture of tacrolimus (TAC) with PEGCCF and TTM.
FIG. 2B depicts DSC thermograms of PEGCCF, TAC, physical mixture of TAC with PEGCCF and TTM.

Crystallization behavior of TAC was evaluated by performing XPRD studies on PEGCCF, TAC, physical mixture of TAC with PEGCCF and lyophilized TTM powder (FIG. 2A). The XPRD patterns showed diffraction peaks from 5° to 20° in pure TAC powder as well as physical mixture, depicting no alteration in the crystalline behavior of TAC when present in the physical mixture. However, TTM lyophilized powder showed diffraction peaks for PEGCCF and no specific diffraction peak of TAC. Thus, it is clearly revealed that TAC was successfully encapsulated into the polymer and exhibited an amorphous nature. DSC thermograms of PEGCCF, TAC, physical mixture of TAC with PEGCCF and TTM lyophilized powder are shown in FIG. 2B. TAC showed a specific peak at 140° C. due to its melting and PEGCCF has a peak at 55° C. Both the PEGCCF and TAC peaks were observed in the physical mixture; however no peak for the TAC was observed in TTM formulation. These results are in concordance with XPRD studies and prove that TAC was successfully encapsulated in the formulation.

Targeted tacrolimus polymeric micelles (TTPM) were also prepared by solvent diffusion evaporation method using PLGA-PEG, PEGCCF, DSPE-PEG2000 and DSPE-PEG2000-RGD. The formulation is intended for a sustained release profile due to the use of PLGA-PEG block copolymer. The particle size of the TTPM was found to be <100 nm. There was no loss of drug assay when filtration through a 0.2μ PES membrane filter was carried out. The entrapment efficiency of the drug formulation was >99%.

Figure 3:
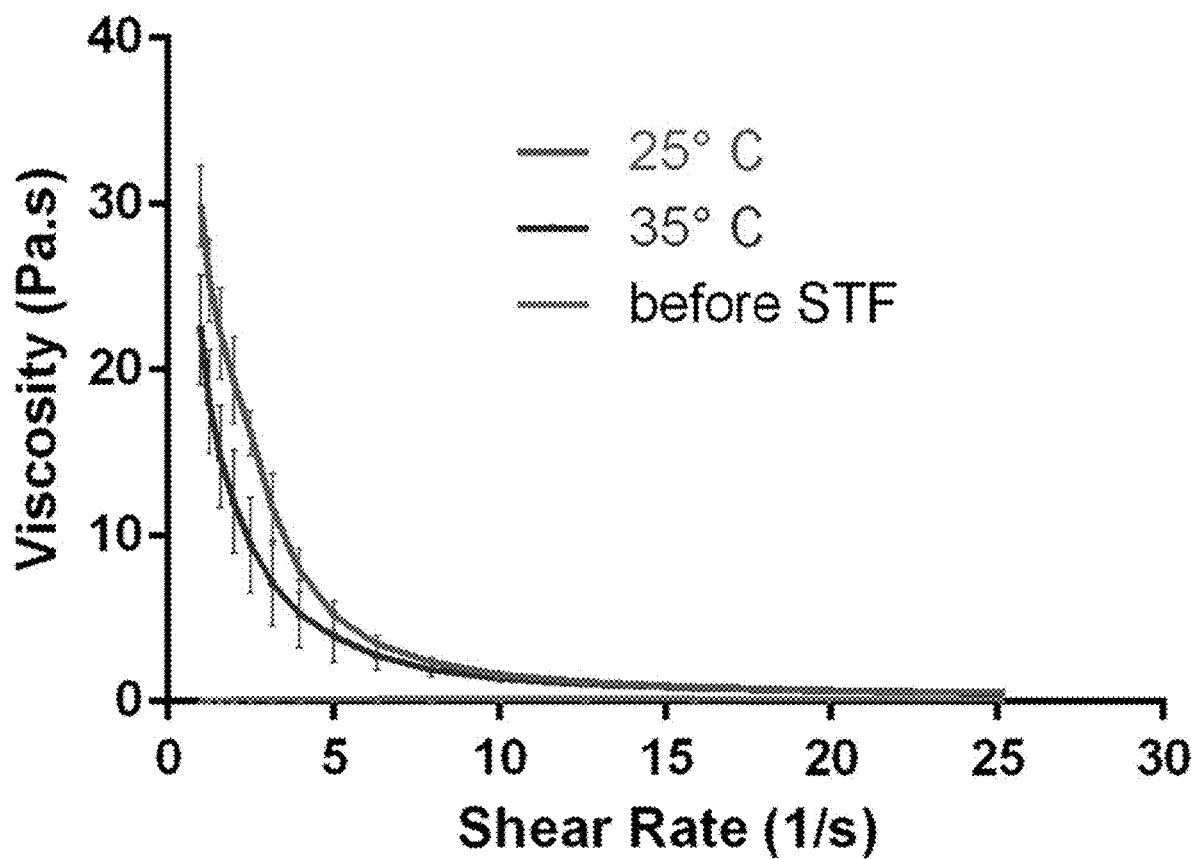
FIG. 3 depicts rheological behavior of 0.5% TTM loaded in situ gel before and after STF treatment. Pink and blue lines represent the rheological data of the in-situ gel after STF treatment at 25° C. and 35° C.

TTPM, due to the solid core, could be loaded in the in-situ gelling formulation to enhance the retention time of the targeted micelles on the ocular surface after administration. The formulation was incorporated in the 0.5% w/v gellan gum. The formulation showed rapid in-situ gelling behavior upon contact with the simulated tear fluid (STF) due to the presence of the divalent cations. The in-situ gel formulation showed sol-to-gel transformation forming a shear-thinning gel with >90% transparency. The rheological behavior of the in-situ gel formulation before and after treatment with simulated tear fluid is shown in FIG. 3. The zero-shear viscosity of the TTPM loaded in situ gelling formulation was <5000 cps (<0.5 Pa·s), which increased to >20000 cps after STF treatment at 35° C.

In-Vivo Evaluation of the Formulation

The effect of formulations was evaluated on BKC-induced ocular surface inflammation in a BALB/c mouse model. BKC disrupts tight junction found on squamous epithelial cells, leading to over-expression of various interleukins (IL-6, IL-10), inflammatory mediators such as ICAM-1 and causes metaplasia of ocular surface. Due to its aforementioned characteristics, BKC mouse model has been reported as appropriate for the studies involving ocular inflammation which correlates to the ocular inflammatory markers involved [12].

Fluorescein Staining of the Cornea

Figure 4:
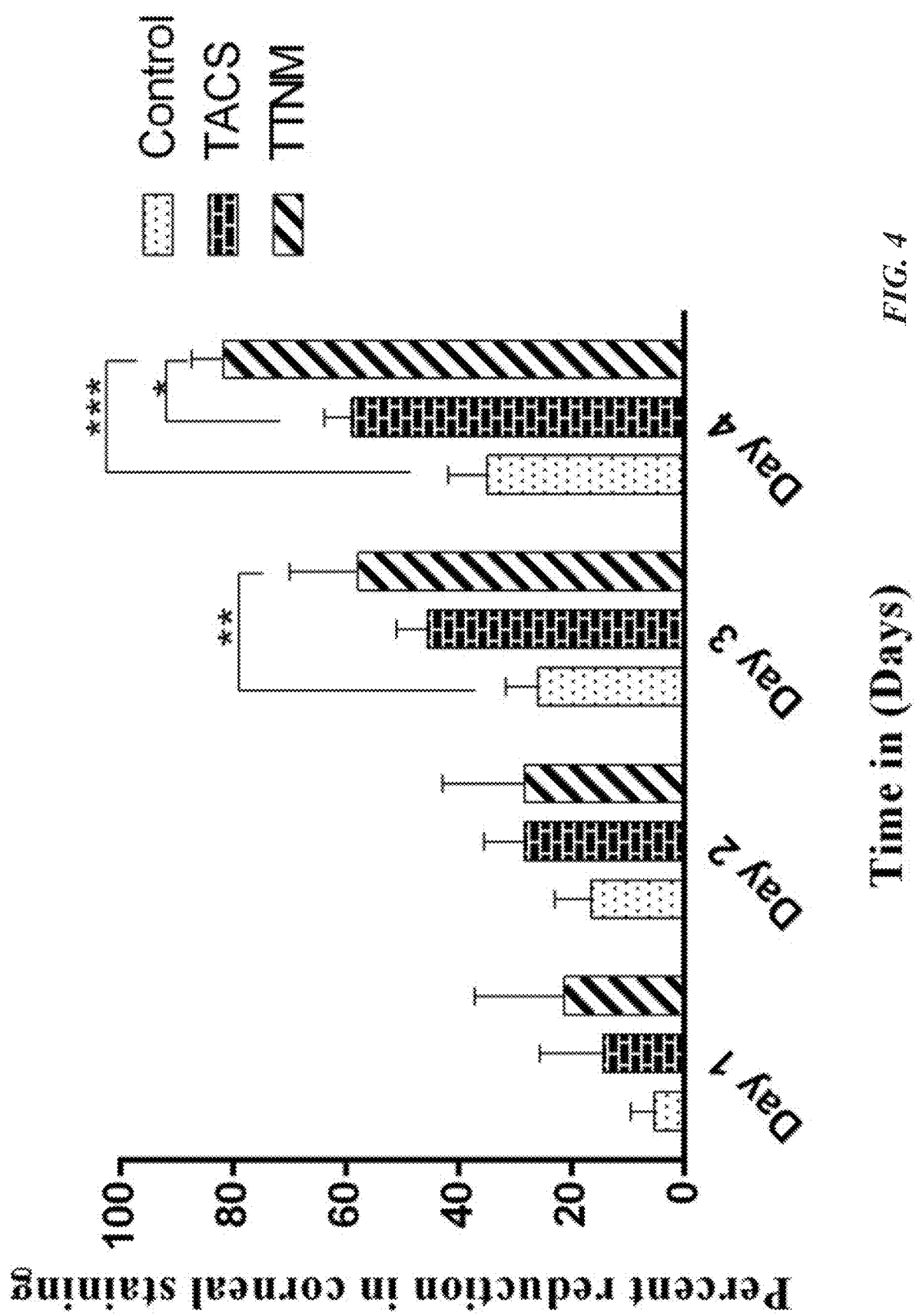
FIG. 4 depicts quantitative estimation of reduction in corneal fluorescein staining after different treatments in a mouse model of ocular surface inflammation. Data shown as mean±SD, * p<0.05, ** p<0.01.

Characterization and quantification of the severity of ocular inflammation were performed by staining with sodium fluorescein. Corneal staining increased progressively in all the mice with highest intensity staining by day 16 of BKC administration. Mice showing >70% fluorescence of the corneal surface were divided in control, TACS and TTM groups and treatments were started with twice a day application of formulations with a once-daily maintenance dose of BKC in between the two administrations of the formulation. Slit-lamp captured fluorescein staining images of the cornea of eyeballs along with a quantitative estimation of the fluorescent area after different treatments are shown in FIG. 4. Corneal fluorescence started declining once treatments were initiated, with a significantly higher reduction in the case of TTM against the control and TACS group. Reduction in corneal staining was higher with TTM compared with TACS ($p<0.05$) and control group ($p<0.001$).

Effect on the Thickness of Different Corneal Layers and Corneal Inflammation

The impact of TTM and TACS was evaluated on the corneal healing by evaluation of corneal thickness. Estimation of the thicknesses of different layers of cornea from H&E stained corneal sections of the mouse eyeballs are shown in FIG. 4. In a normal mouse eye, the thickness of epithelium in the central, peripheral and limbal region is 43.2±10μ, 27.4±11μ and 17.2±5μ respectively. However, corneal epithelium thickness in control was observed as 21.3±13μ, 19.2±14μ and 18.3±18μ in central, peripheral, and limbal region respectively. Also, the stromal thickness in the normal eye is about 76.5±5μ, 70±10.1μ and 60.2±5μ while the stromal thickness noticed in control was 160.3±23μ, 140.4±16μ and 80.3±20μ in central, peripheral, and limbal region respectively. Thus, it can be seen, BKC led to a reduction in corneal epithelial thickness along with remarkable edema in the stromal region in both central and peripheral regions (FIG. 4).

Figure 5A:
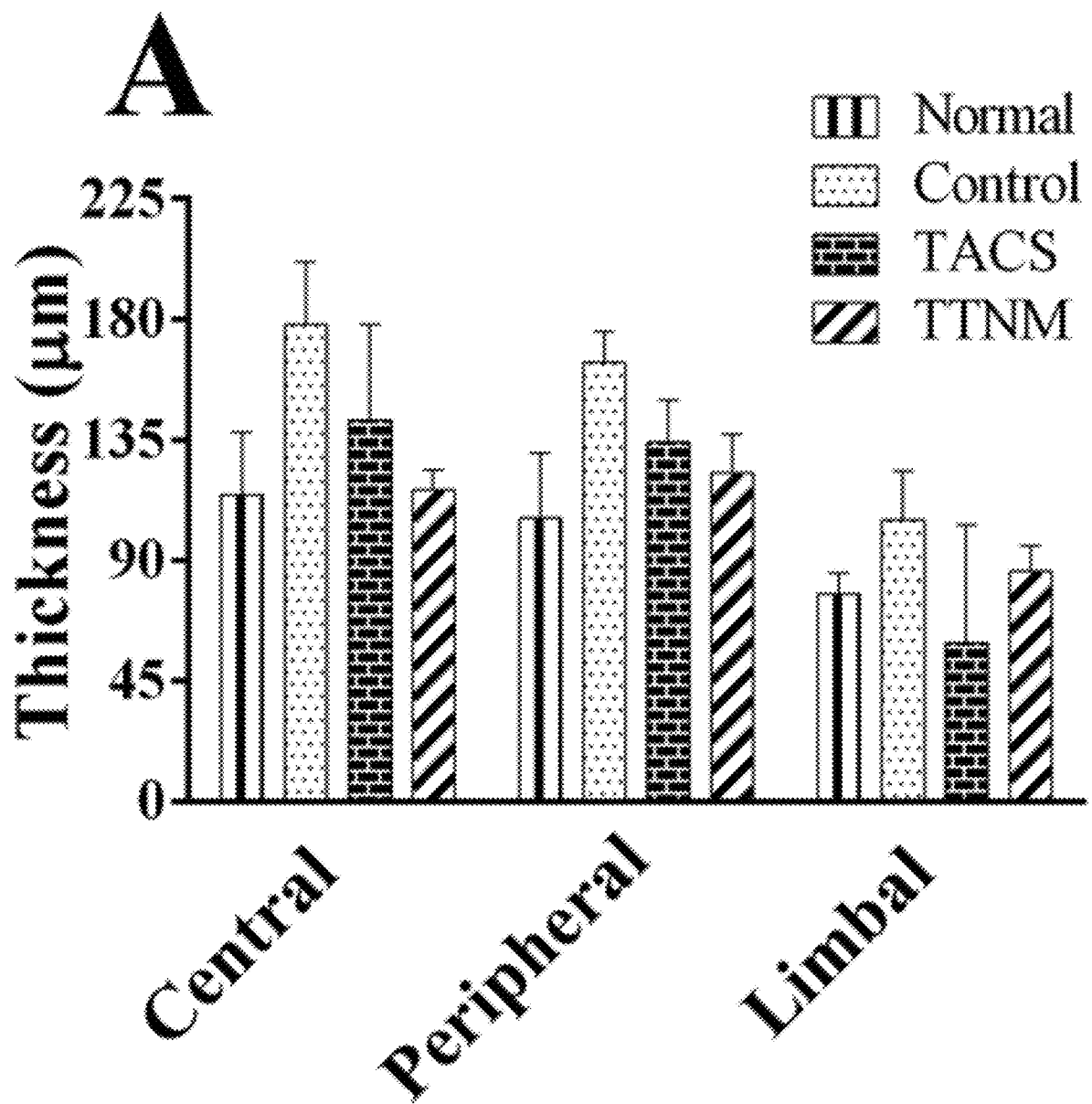
FIG. 5A depicts an assessment of corneal integrity through H&E staining after different treatment depicting results with total corneal thickness. Data shown as mean±SD, * p<0.05. Normal=normal mouse eye, Control=model control, TACS and TTM=treatment groups.
Figure 5B:
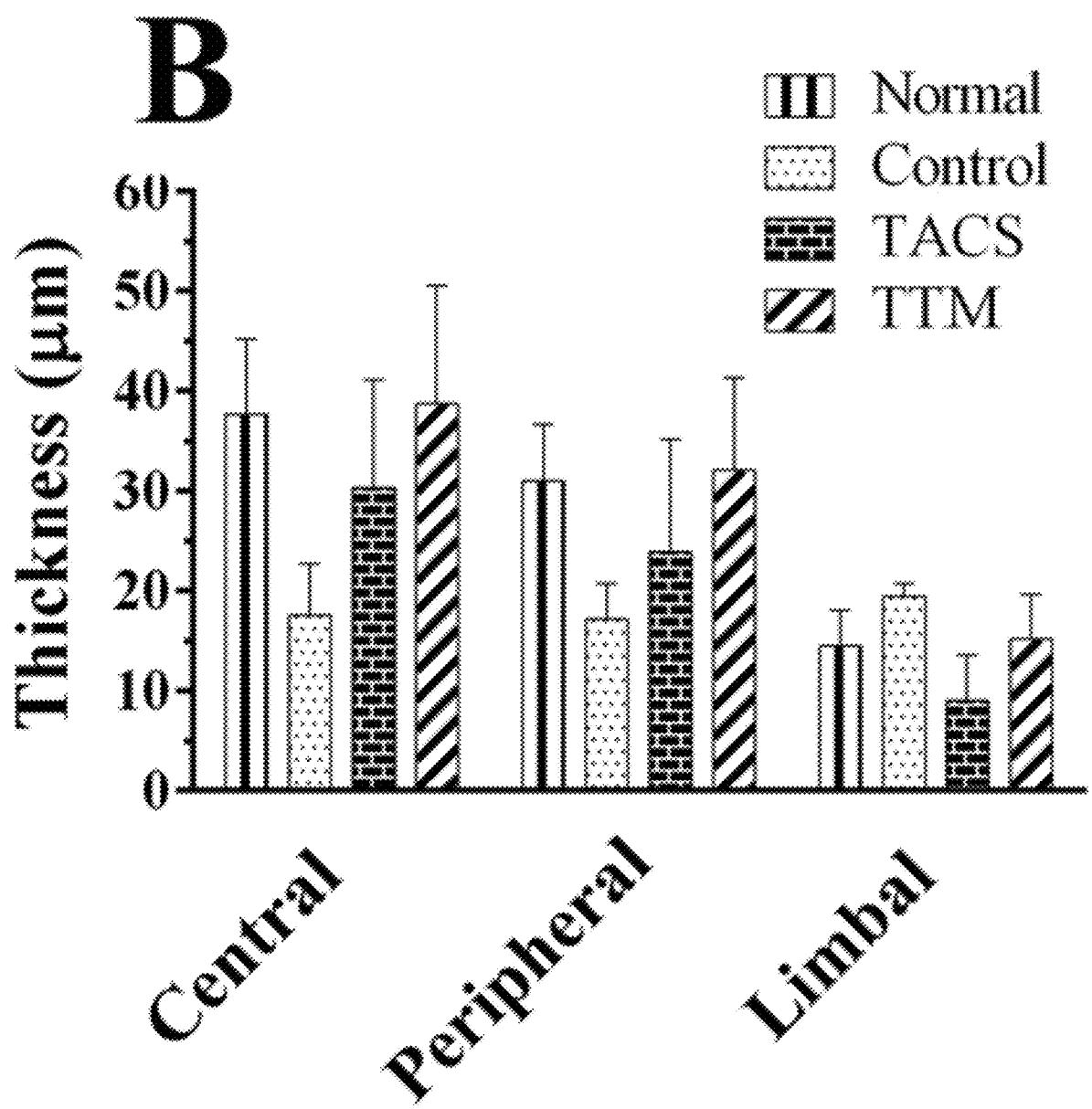
FIG. 5B depicts an assessment of corneal integrity through H&E staining after different treatment depicting with epithelial thickness. Data shown as mean±SD, * p<0.05. Normal=normal mouse eye, Control=model control, TACS and TTM=treatment groups.
Figure 5C:
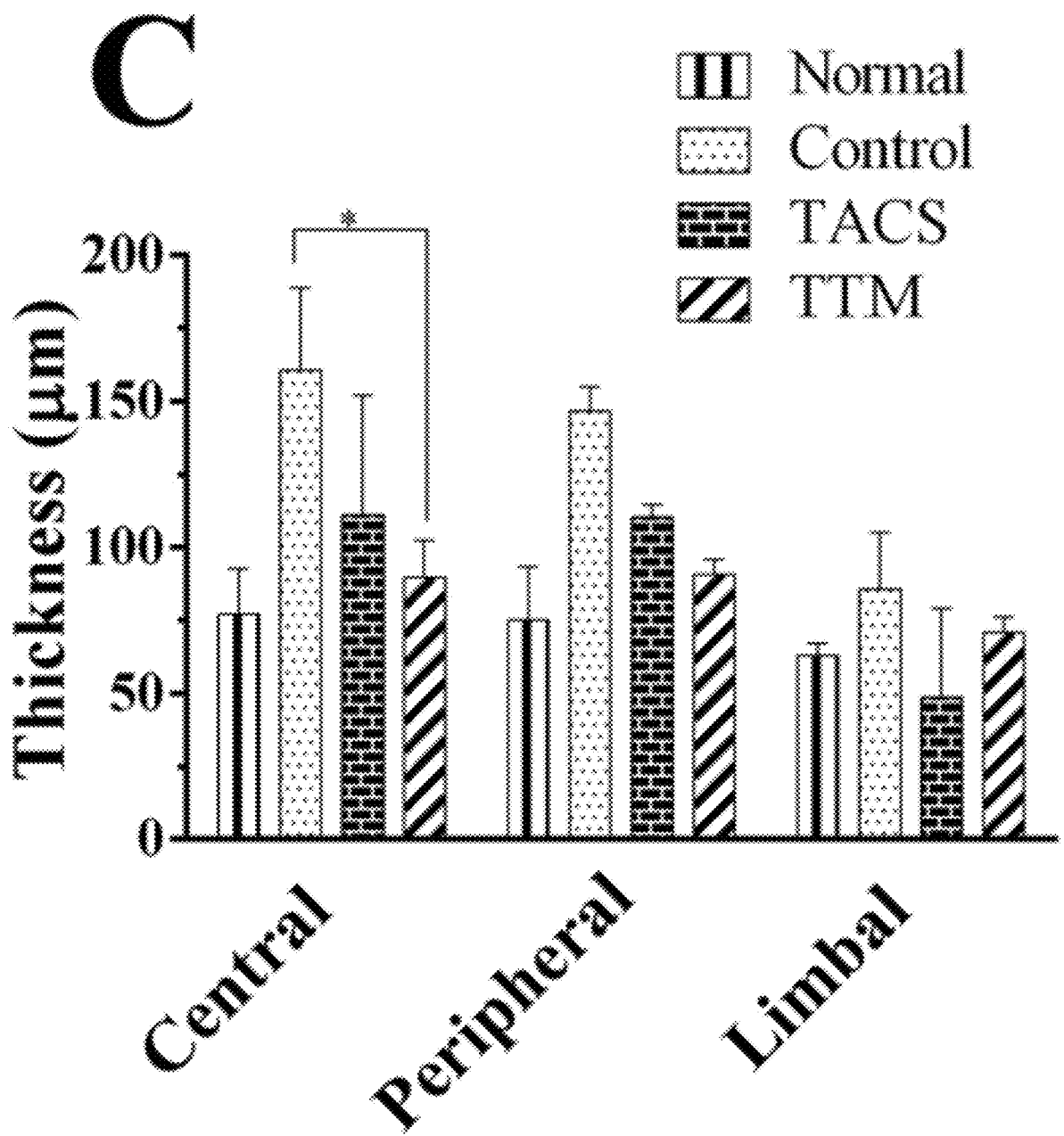
FIG. 5C depicts an assessment of corneal integrity through H&E staining after different treatment depicting results with stromal thickness. Data shown as mean±SD, * p<0.05. Normal=normal mouse eye, Control=model control, TACS and TTM=treatment groups.
Figure 6:
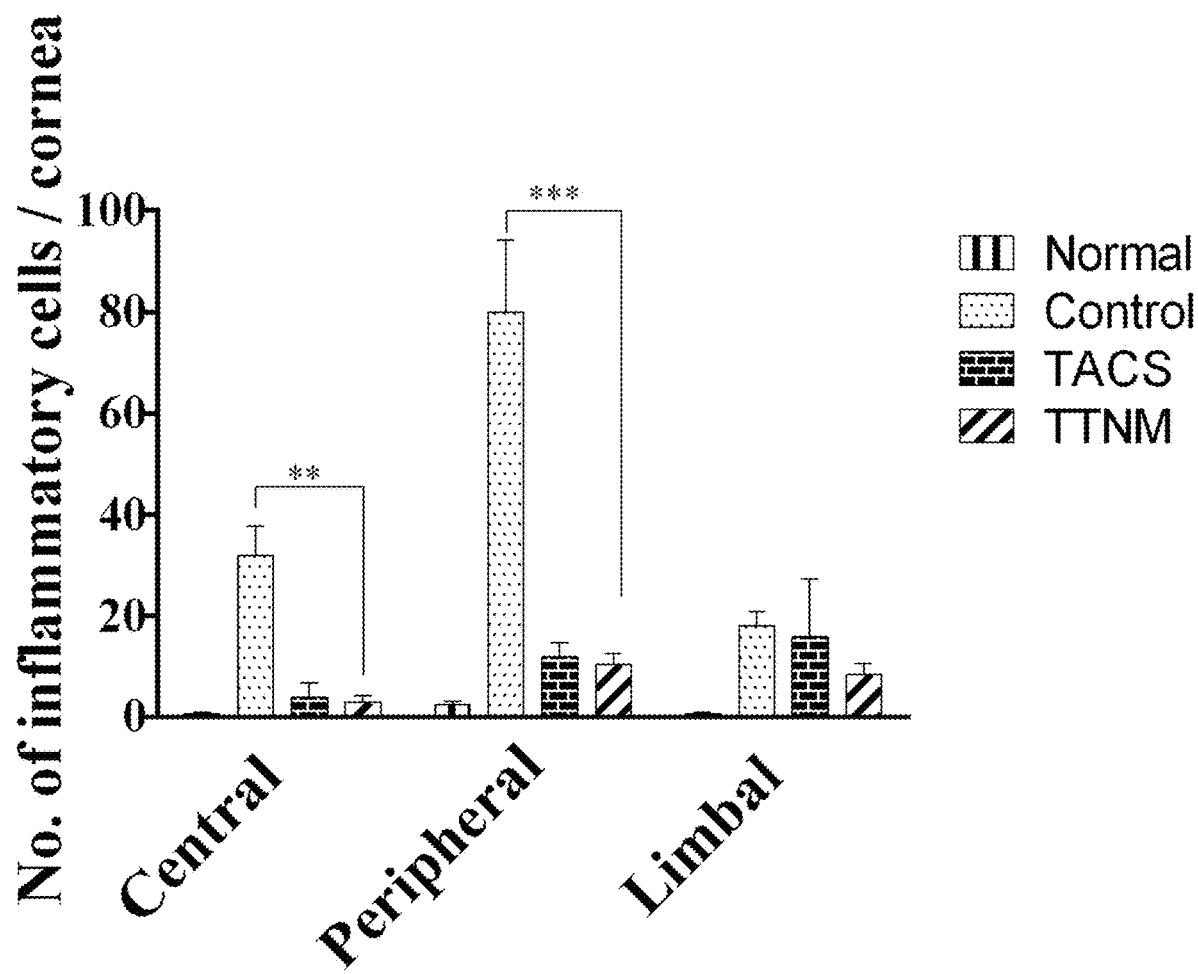
FIG. 6 depicts the number of inflammatory cells in different regions of the cornea. TTM reduced the number of inflammatory cells. Data shown as mean±SD,  p<0.01 and *p<0.001; Control=model control, treatment groups=TACS and TTM.

Severe damage to the corneal epithelium by BKC also led to extensive loss as well as edema of stromal region. Stromal thickness observed in the H&E staining is due to a combination of edema of the stromal region (as can be seen from the edematous pockets in the stroma) because of the infiltration of the immune cells and fluid accumulation and the loss of stromal cells by BKC. TTM improved epithelial thickness (FIG. 5B) and decreased stromal thickness compared with control ($p<0.05$) and TACS while the H&E staining shows reduced numbers of edematous pockets in stroma indicating that the stromal cell density in stromal regions is being restored with concomitant reduction in stromal edema (FIG. 5C) indicating the ongoing healing process rather than complete healing. Hence, TM restored the overall corneal thickness (FIG. 5A). Furthermore, TTM significantly reduced the infiltration of inflammatory cells in peripheral and central corneal regions (FIG. 6). In contrast, TACS does not provide much improvement in stromal healing.

Effect on Proliferation Marker Ki67 and Inflammatory Marker IL-6

Figure 7A:
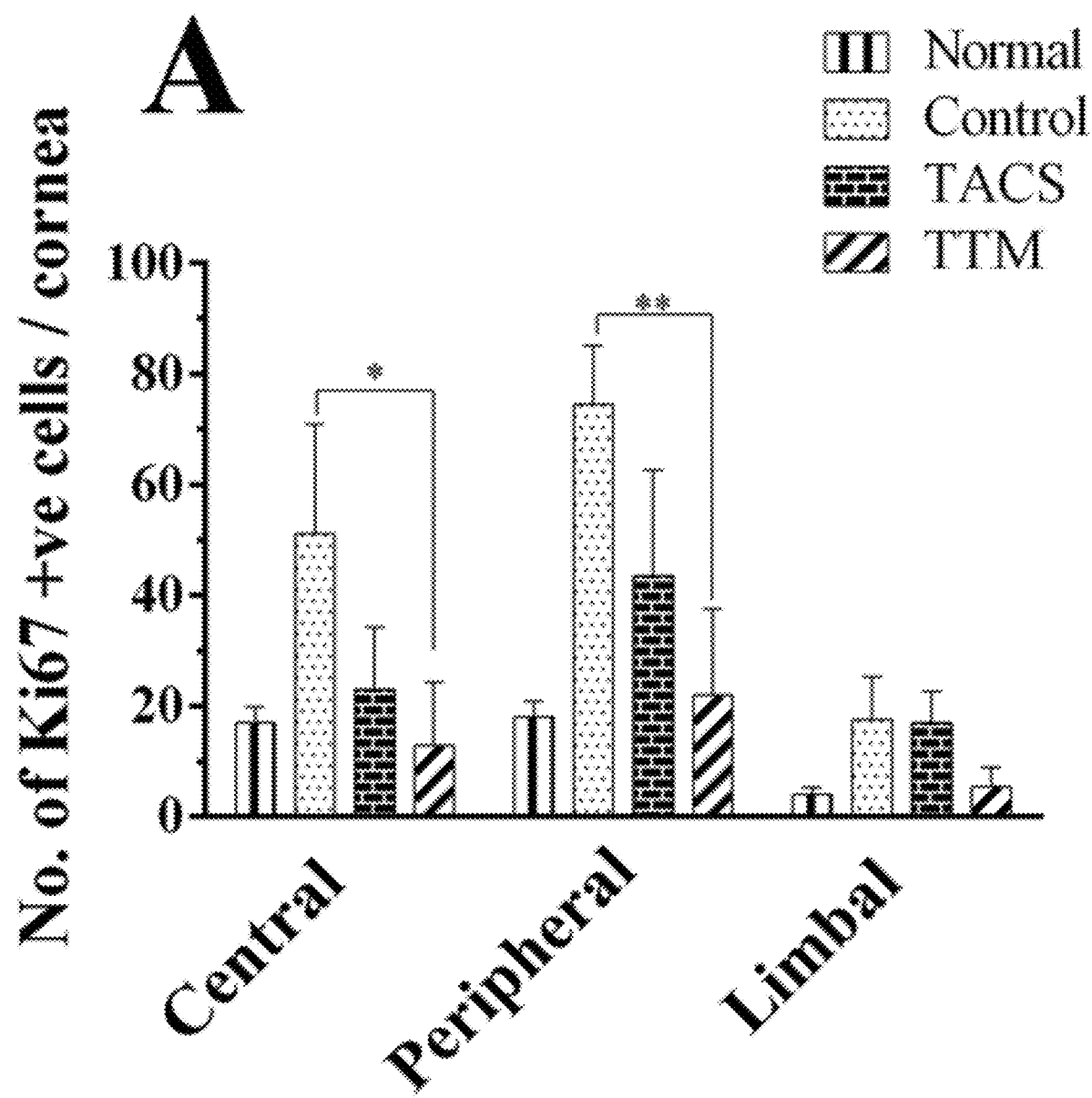
FIG. 7A depicts immunohistochemical analysis of Ki67 expression after different treatments showing quantitative analysis of Ki67 positive cells in the whole cornea. Data shown as mean±SD, * p<0.05,  p<0.01 and *p<0.001; Control=model control, treatment groups=TACS and TTM.
Figure 7B:
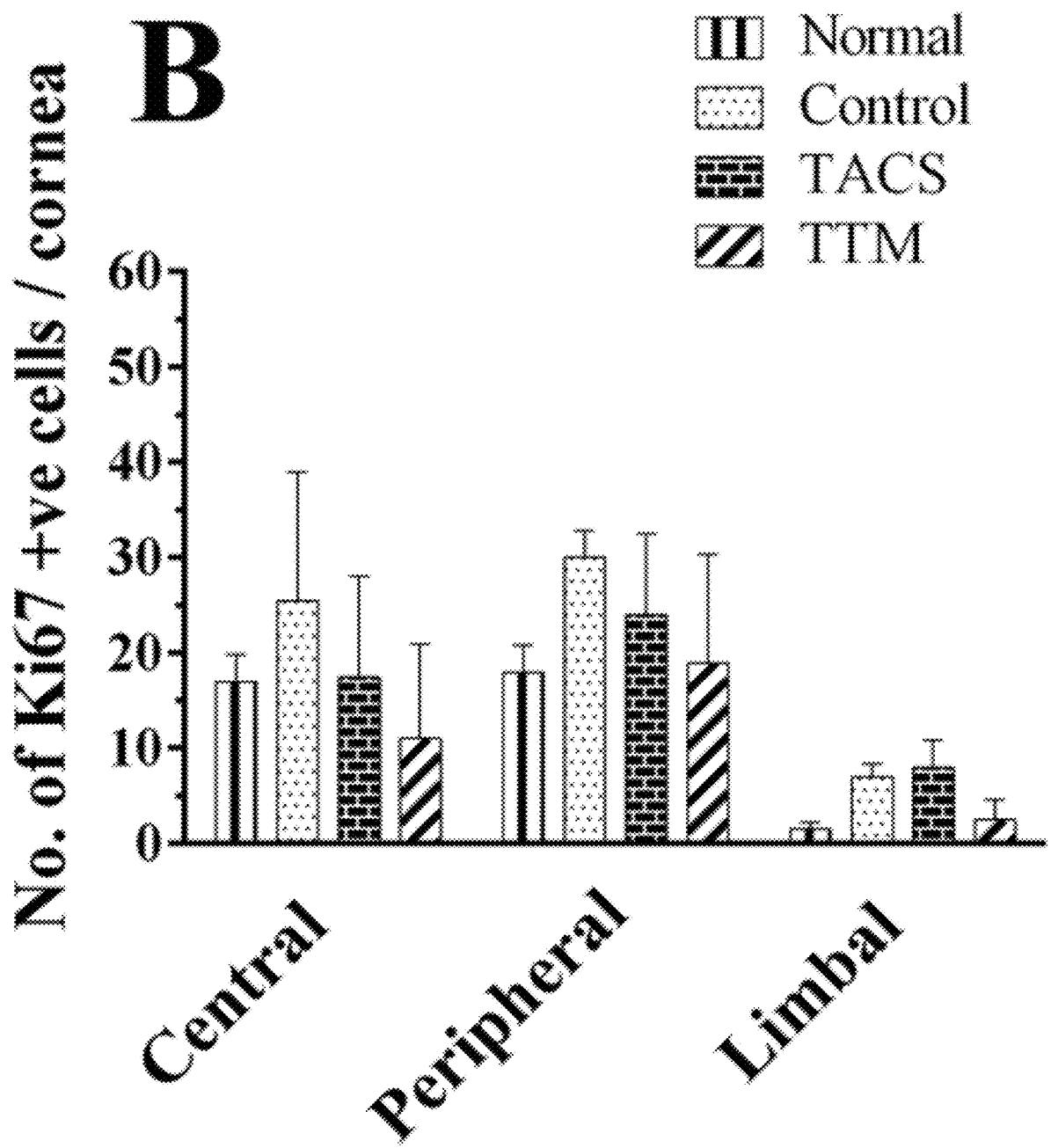
FIG. 7B depicts immunohistochemical analysis of Ki67 expression after different treatments showing quantitative analysis of Ki67 positive cells in the corneal epithelium. Data shown as mean±SD, * p<0.05,  p<0.01 and *p<0.001; Control=model control, treatment groups=TACS and TTM.
Figure 7C:
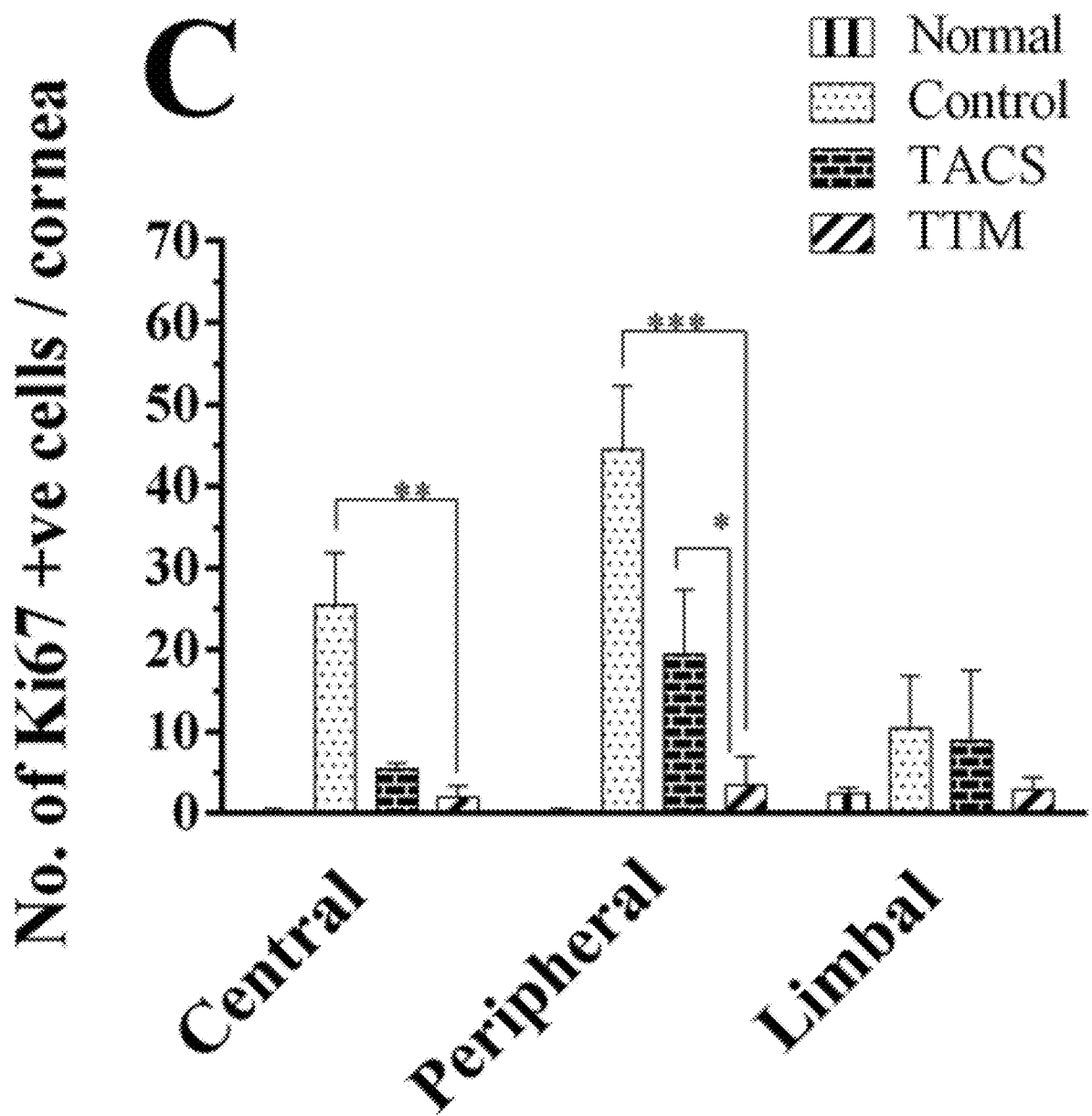
FIG. 7C depicts immunohistochemical analysis of Ki67 expression after different treatments showing quantitative analysis of Ki67 positive cells in the corneal stroma. Data shown as mean±SD, * p<0.05,  p<0.01 and *p<0.001; Control=model control, treatment groups=TACS and TTM.
Figure 8A:
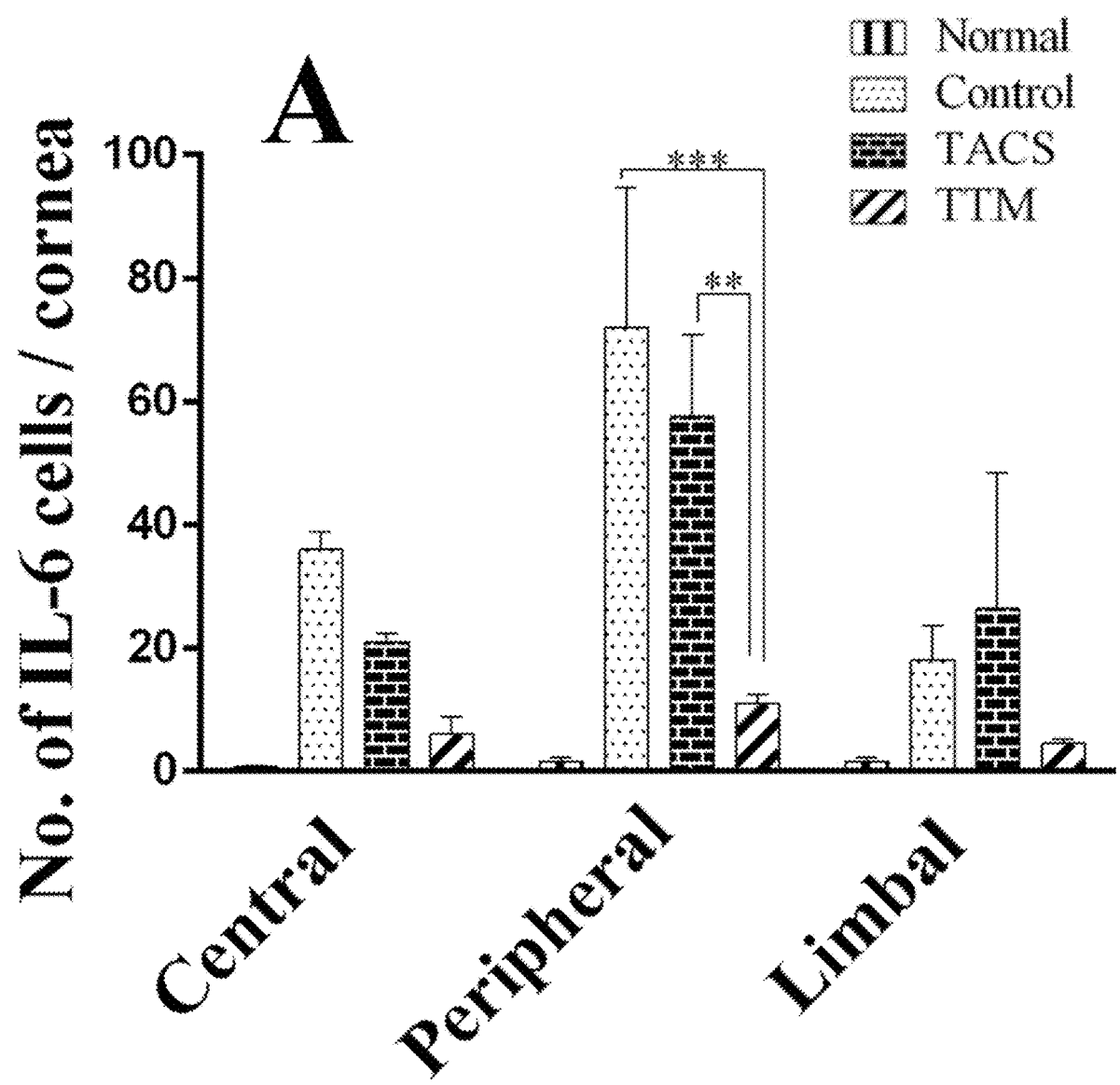
FIG. 8A depicts immunohistochemical analysis of IL-6 expression after different treatments showing quantitative analysis of IL-6 positive cells in the whole cornea. Data shown as mean±SD, * p<0.05,  p<0.01 and *p<0.001; Control=model control, treatment groups=TACS and TTM.
Figure 8B:
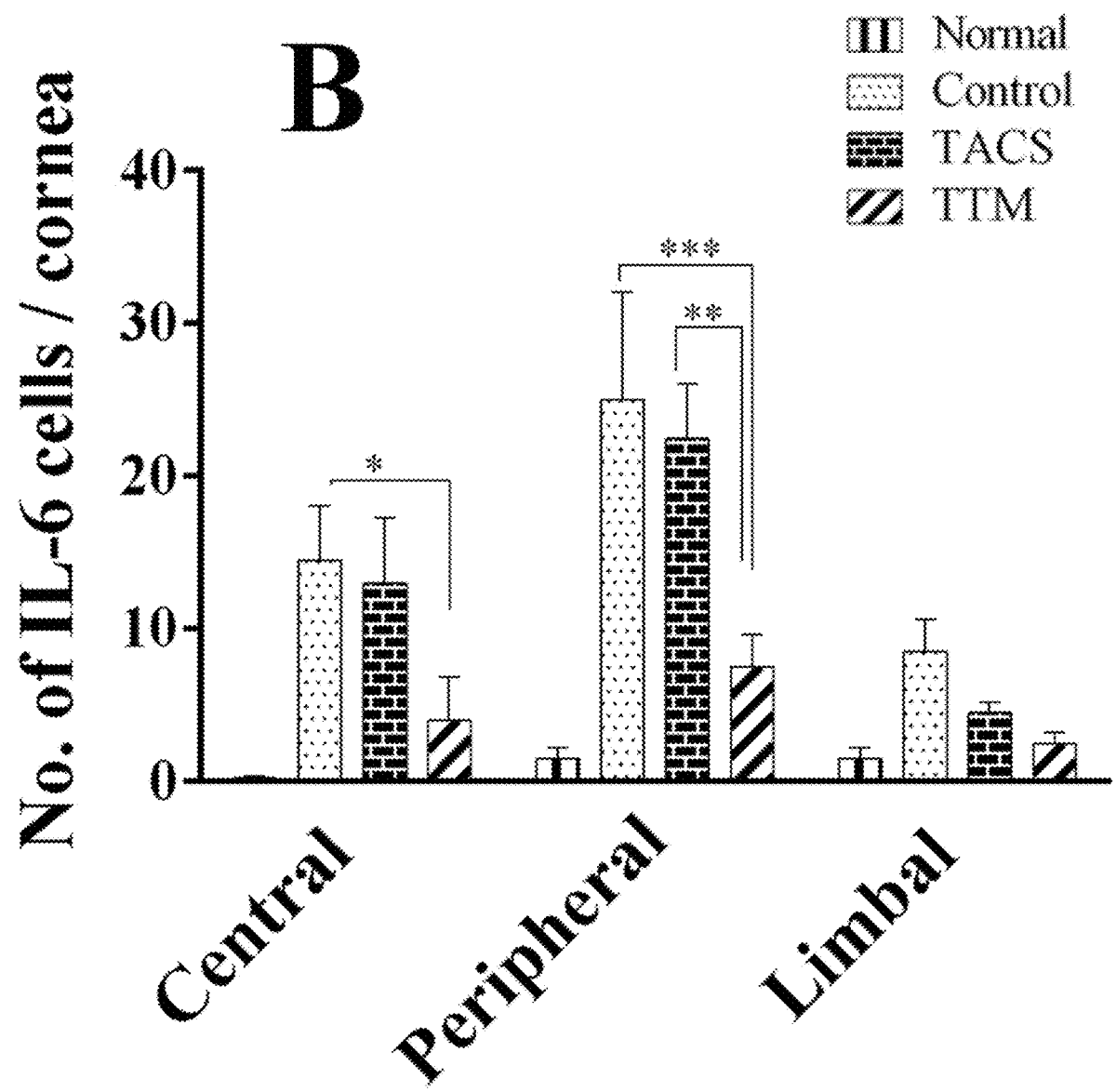
FIG. 8B depicts immunohistochemical analysis of IL-6 expression after different treatments showing quantitative analysis of IL-6 positive cells in the corneal epithelium. Data shown as mean±SD, * p<0.05,  p<0.01 and *p<0.001; Control=model control, treatment groups=TACS and TTM.
Figure 8C:
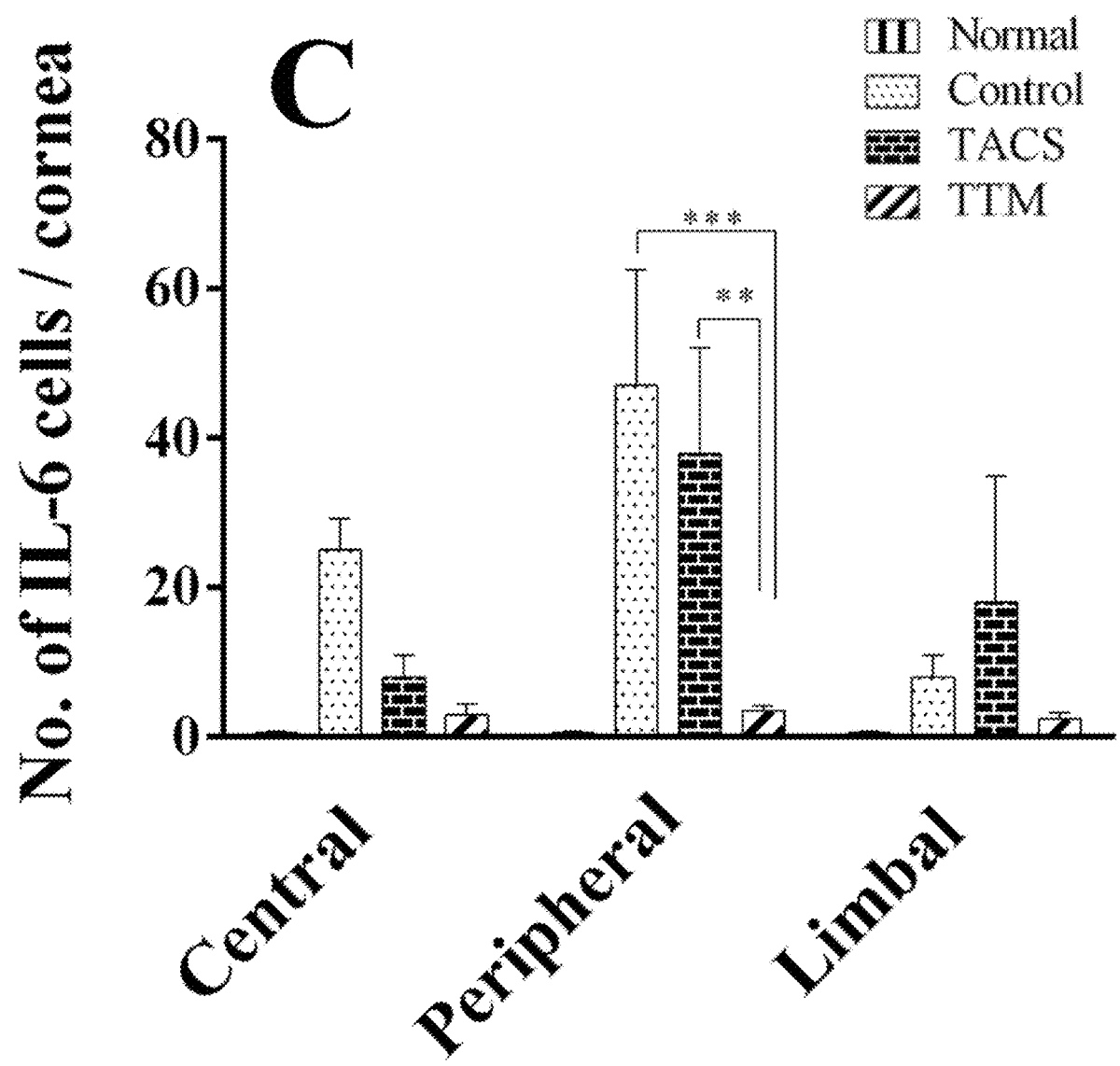
FIG. 8C depicts immunohistochemical analysis of IL-6 expression after different treatments showing quantitative analysis of IL-6 positive cells in the corneal stroma. Data shown as mean±SD, * p<0.05,  p<0.01 and *p<0.001; Control=model control, treatment groups=TACS and TTM.

Immunohistochemical analyses of corneal sections for expression of proliferation and differentiation marker Ki67 and inflammatory marker IL-6 revealed that BKC damage led to significant expression of both Ki67 positive cells and IL-6 on the corneal surface, bulbar conjunctival and limbal region as compared to the normal eye (FIGS. 7A-7C and 8A-8C). As shown in FIGS. 7A-7C, expression of Ki67 cells on central and peripheral region was significantly lower in TTM group as compared to control ($p<0.05$) and TACS group ($p<0.05$). While IL-6 expression was reduced throughout the cornea, a significant reduction in the peripheral corneal regions of TTM group was observed (FIGS. 8A-8C) when compared to TACS ($p<0.01$) and control ($p<0.001$). TACS provides some reduction in the Ki67 and IL-6 expression which was statistically significant ($p<0.05$) compared with the control group which was, however, significantly lower than that observed with TTM.

REFERENCES

[1] G. D. Kymionis, D. I. Bouzoukis, V. F. Diakonis, C. Siganos, Treatment of chronic dry eye: focus on cyclosporine, Clinical Ophthalmology (Auckland, N. Z.), 2 (2008) 829-836.

[2] P. Taravati, D. L. Lam, T. Leveque, R. N. Van Gelder, Postcataract surgical inflammation, Current opinion in ophthalmology, 23 (2012) 12-18.

[3] D. R. Harminder, Attre, Treatment of Post-operative Inflammation following Cataract Surgery—A Review, European Ophthalmic Review, 6 (2012) 98-103.

[4] P. Saha, J. J. Yang, V. H. Lee, Existence of a p-glycoprotein drug efflux pump in cultured rabbit conjunctival epithelial cells, Investigative ophthalmology & visual science, 39 (1998) 1221-1226.

[5] K. Kawazu, K. Yamada, M. Nakamura, A. Ota, Characterization of cyclosporin A transport in cultured rabbit corneal epithelial cells: P-glycoprotein transport activity and binding to cyclophilin, Investigative ophthalmology & visual science, 40 (1999) 1738-1744.

[6] S. Dey, S. Gunda, A. K. Mitra, Pharmacokinetics of erythromycin in rabbit corneas after single-dose infusion: role of P-glycoprotein as a barrier to in vivo ocular drug absorption, The Journal of pharmacology and experimental therapeutics, 311 (2004) 246-255.

[7] S. Dey, J. Patel, B. S. Anand, B. Jain-Vakkalagadda, P. Kaliki, D. Pal, V. Ganapathy, A. K. Mitra, Molecular evidence and functional expression of P-glycoprotein (MDR1) in human and rabbit cornea and corneal epithelial cell lines, Investigative ophthalmology & visual science, 44 (2003) 2909-2918.

[8] M. A. Stepp, Corneal integrins and their functions, Experimental eye research, 83 (2006) 3-15; S. G. Elner, V. M. Elner, The integrin superfamily and the eye, Investigative ophthalmology & visual science, 37 (1996) 696-701.

[9] B. Lauweryns, J. J. van den Oord, R. Volpes, B. Foets, L. Missotten, Distribution of very late activation integrins in the human cornea. An immunohistochemical study using monoclonal antibodies, Investigative ophthalmology & visual science, 32 (1991) 2079-2085.

[10] K. Ley, J. Rivera-Nieves, W. J. Sandborn, S. Shattil, Integrin-based therapeutics: biological basis, clinical use and new drugs, Nat Rev Drug Discov, 15 (2016) 173-183.

[11] K. Kunath, T. Merdan, O. Hegener, H. Haberlein, T. Kissel, Integrin targeting using RGD-PEI conjugates for in vitro gene transfer, The journal of gene medicine, 5 (2003) 588-599.

[12] Z. Lin, X. Liu, T. Zhou, Y. Wang, L. Bai, H. He, Z. Liu, A mouse dry eye model induced by topical administration of benzalkonium chloride, 2011.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. An ophthalmic composition comprising:
   at least one targeted micelle comprising
      poly(ethylene glycol) methyl ether 2000 (PEG2000) conjugated with cholecalciferol to form PEGCCF;
      1,2-distearoyl-sn-glycero-3-phosphoethanolamine-N-[methoxy (polyethylene glycol)-2000] (DSPE-PEG2000); and
      DSPE-PEG2000 conjugated to arginine-glycine-aspartic acid peptide (RGD) to form DSPE-PEG2000-RGD;
   an amount of tacrolimus encapsulated within the at least one targeted micelle; and
   a pharmaceutically acceptable carrier.

2. The ophthalmic composition of claim 1, wherein the at least one targeted micelle further comprises poly(lactic acid-co-glycolic acid)-poly(ethylene glycol) (PLGA-PEG) block copolymer to form at least one targeted tacrolimus polymeric micelle (TTPM).

3. The ophthalmic composition of claim 2, wherein the pharmaceutically acceptable carrier is gellan gum.

4. The ophthalmic composition of claim 3, wherein the tacrolimus is sustainably released from the composition.

5. The ophthalmic composition of claim 3, wherein the at least one targeted tacrolimus polymeric micelle has a drug entrapment efficiency greater than 99%.

6. The ophthalmic composition of claim 3, wherein the at least one targeted tacrolimus polymeric micelle has a particle size of less than about 100 nm.

7. The ophthalmic composition of claim 1, wherein the at least one targeted micelle has a particle size less than about 50 nm.

8. The ophthalmic composition of claim 1, wherein the at least one targeted micelle is prepared by solvent diffusion evaporation.

9. A composition for treating or reducing ocular surface inflammation comprising:
   at least one targeted tacrolimus polymeric micelle (TTPM) comprising
      poly(ethylene glycol) methyl ether 2000 (PEG2000) conjugated with cholecalciferol to form PEGCCF;
      1,2-distearoyl-sn-glycero-3-phosphoethanolamine-N-[methoxy (polyethylene glycol)-2000] (DSPE-PEG2000);
      DSPE-PEG2000 conjugated to arginine-glycine-aspartic acid peptide (RGD) to form DSPE-PEG2000-RGD; and
      poly(lactic acid-co-glycolic acid)-poly(ethylene glycol) (PLGA-PEG) block copolymer;
   an amount of tacrolimus encapsulated within the at least one targeted micelle; and
   a pharmaceutically acceptable carrier;
   wherein the tacrolimus is sustainably released from the composition.

10. The composition of claim 9, wherein the pharmaceutically acceptable carrier is gellan gum.

11. The composition of claim 9, wherein the at least one targeted tacrolimus polymeric micelle has a particle size of less than about 100 nm.

12. The composition of claim 9, wherein the at least one tacrolimus polymeric micelle has a drug entrapment efficiency of greater than 99%.

13. A method of treating or reducing ocular surface inflammation comprising:
   administering a therapeutically effective amount of a composition comprising
      at least one targeted micelle comprising
         poly(ethylene glycol) methyl ether 2000 (PEG2000) conjugated with cholecalciferol to form PEGCCF;
         1,2-distearoyl-sn-glycero-3-phosphoethanolamine-N-[methoxy (polyethylene glycol)-2000] (DSPE-PEG2000); and
         DSPE-PEG2000 conjugated to arginine-glycine-aspartic acid peptide (RGD) to form DSPE-PEG2000-RGD;
      an amount of tacrolimus encapsulated within the at least one targeted micelle; and
      a pharmaceutically acceptable carrier.

14. The method of claim 13, wherein the at least one micelle has a particle size of less than about 50 nm.

15. The method of claim 13, wherein the composition is administered twice per day.

16. The method of claim 13, wherein the at least one targeted micelle further comprises poly(lactic acid-co-glycolic acid)-poly(ethylene glycol) (PLGA-PEG) block copolymer to form at least one targeted tacrolimus polymeric micelle (TTPM).

17. The method of claim 16, wherein the pharmaceutically acceptable carrier is gellan gum.

18. The method of claim 17, wherein the at least one targeted tacrolimus polymeric micelle has a particle size of less than about 100 nm.

19. The method of claim 17, wherein the at least one targeted tacrolimus polymeric micelle has a drug entrapment efficiency of greater than about 99%.

20. The method of claim 17, wherein the tacrolimus is sustainably released from the composition.

* * * * *